United States Patent [19]

Miyazaki et al.

[11] Patent Number: 4,511,744

[45] Date of Patent: Apr. 16, 1985

[54] PROCESS FOR PRODUCING LOWER ALKYLENE GLYCOL, CATALYST COMPOSITION USED THEREFOR AND PROCESS FOR PRODUCTION THEREOF

[75] Inventors: Haruhiko Miyazaki; Koichi Hirai; Taizo Uda; Yasuo Nakamura, all of Ube; Harumi Ikezawa, Onoda; Takanori Tsuchie, Ube, all of Japan

[73] Assignee: UISE Industries, Ltd., Yamaguchi, Japan

[21] Appl. No.: 491,742

[22] Filed: May 5, 1983

[30] Foreign Application Priority Data

May 6, 1982 [JP] Japan ................................. 57-74611

[51] Int. Cl.$^3$ ..................... C07C 29/136; C07C 31/20
[52] U.S. Cl. .................................... 568/864; 502/244
[58] Field of Search ........................................ 568/864

[56] References Cited

U.S. PATENT DOCUMENTS 2,305,104 12/1942 Pardee ................................. 568/864
4,283,581 8/1981 Wilker ................................ 568/864

FOREIGN PATENT DOCUMENTS 575380 2/1946 United Kingdom ................ 568/864

Primary Examiner—J. E. Evans
Attorney, Agent, or Firm—Sherman & Shalloway

[57] ABSTRACT

A hydrogenation catalyst composition for use in the hydrogenation of a lower alkyl ester of a lower hydroxycarboxylic acid. The composition is composed of a reduction product of copper-containing silica gel formed by contacting an ammine complex of copper with silica gel having an average particle diameter of not more than 200 microns or colloidal silica sol. A process for producing the catalyst composition is also provided. By using the aforesaid catalyst composition, a lower alkylene glycol can be produced efficiently in high conversions and selectivities without causing pollution attributed to the use of a chromium-containing catalyst composition.

14 Claims, No Drawings

PROCESS FOR PRODUCING LOWER ALKYLENE GLYCOL, CATALYST COMPOSITION USED THEREFOR AND PROCESS FOR PRODUCTION THEREOF

This invention relates to a commercial process for producing a lower alkylene glycol such as ethylene glycol, propylene glycol, butanediol, etc. from a lower alkyl ester of a lower hydroxycarboxylic acid efficiently in high conversions and selectivities without causing pollution attributed to the use of a chromium-containing catalyst composition.

The invention also relates to a catalyst composition for use in the aforesaid process, and to a process for producing the catalyst composition.

More specifically, this invention relates to a hydrogenation catalyst composition for use in the hydrogenation of a lower alkyl ester of a lower hydroxycarboxylic acid, composed of a reduction product of copper-containing silica gel formed by contacting an ammine complex of copper with silica gel having an average particle diameter of not more than 200 microns or colloidal silica sol.

The catalyst composition can be prepared by contacting an ammine complex of copper with silica gel having an average particle diameter of not more than 200 microns or colloidal silica sol in the presence of an aqueous medium to form copper-containing silica gel, and subjecting the copper-containing silica gel to a reducing treatment. This invention also pertains to a process for producing a lower alkylene glycol, which comprises hydrogenating a lower alkyl ester of a lower hydroxycarboxylic acid in the vapor or gaseous phase at an elevated temperature in the presence of the aforesaid catalyst composition.

It is known to prepare an alkylene glycol by the catalytic hydrogenation of an alkyl ester of a hydroxycarboxylic acid in the vapor or gaseous phase at an elevated temperature in the presence of a hydrogenation catalyst, and Cu/Cr type catalysts have already been proposed as the hydrogenation catalyst.

For example, British Patent Specification No. 575,380 proposes the use of a copper-chromium type catalyst or a copper-silica catalyst obtained by melting copper oxide and silicon dioxide, as a hydrogenation catalyst.

U.S. Pat. No. 2,093,159 suggests the use of a copper catalyst containing an activating substance (oxoacid salt) of chromium, molybdenum or tungsten.

U.S. Pat. No. 2,094,611 discloses the use of a copper-chromium type catalyst.

Methods involving using these known hydrogenation catalysts have one or more defects. For example, they may be directed mainly to the hydrogenation of higher hydroxycarboxylic acid esters. The hydrogenation reaction must be carried out under a high pressure of at least 10 atmospheres. The catalyst system is complex. Or the yield and selectivity of the desired product are not entirely satisfactory.

Cu/Cr type catalysts are generally known to be useful for hydrogenating esters to the corresponding alcohols. In the aforesaid catalytic hydrogenation of an alkyl ester of a hydroxycarboxylic acid, too, the use of copper-chromium type catalysts prevails. The use of such chromium-containing catalysts causes troubles from a practical viewpoint. It is extremely difficult, if not impossible by a complicated and expensive operation, to recover chromium efficiently and completely from a spent Cu/Cr type catalyst, and such a catalyst is not suitable for industrial operations. Since chromium, even in trace, exhibits strong toxicity to humans, discarding of chromium-containing catalyst residues in general environments should be avoided. This leads to the defect that the relatively good catalytic activity of the Cu/Cr type catalysts is reduced in practice because of the difficulty of disposing of the spent catalysts.

It is generally known that various other metals or metal compounds can be used as hydrogenation catalysts or their components. Examples include Raney nickel, nickel, cobalt, copper, iron, platinum, and palladium, and their oxides and sulfides. It is well known that these generally known metals or metal compounds are not necessarily useful in all catalytic hydrogenation reactions, and a desired hydrogenation reaction cannot be carried out efficiently unless a catalyst suitable for the desired hydrogenation is selected according to the mode of the reaction, the hydrogenation reaction conditions, etc. It is also widely known that no established guideline exists for selecting such a suitable catalyst.

We have extensively worked in order to develop a catalyst composition for the catalytic hydrogenation of a lower alkyl ester of a lower hydroxycarboxylic acid, which is free from chromium and has better catalytic activity that that of conventional catalysts for the catalytic hydrogenation of a hydroxycarboxylic acid ester.

We have consequently found that a catalyst composition composed of a reduction product of copper-containing silica gel formed by contacting an ammine complex of copper with silica gel having an average particle diameter of not more than 200 microns or colloidal silica sol is useful for preparing a lower alkylene glycol efficiently from a lower alkyl ester of a lower hydroxycarboxylic acid in higher conversions and selectivities with industrial advantage than the known Cu-Cr catalysts, and can overcome the trouble of conventional chromium-containing catalyst compositions. It has also been found that this catalyst can be prepared by contacting an ammine complex of copper with silica gel having an average particle diameter of not more than 200 microns or colloidal silica sol to form copper-containing silica gel, and subjecting the resultant copper-containing silica gel to a reducing treatment.

It is an object of this invention therefore to provide a hydrogenation catalyst composition for the hydrogenation of a lower alkyl ester of a lower hydroxycarboxylic acid.

A second object of this invention is to provide a process for producing the aforesaid hydrogenation catalyst.

A third object of this invention is to provide a process for producing a lower alkylene glycol from a lower alkylester of a lower hydroxycarboxylic acid in the presence of the aforesaid hydrogenation catalyst.

The above and other objects and advantages of this invention will become more apparent from the following description.

The hydrogenation catalyst composition of this invention can be produced by a process which comprises contacting an ammine complex of copper with silica gel having an average particle diameter of not more than 200μ or colloidal silica sol, and subjecting the resulting copper-containing silica gel to reduction.

According to its one embodiment, an aqueous solution containing an ammine complex of copper is mixed with colloidal silica sol. At this stage, the silica sol changes to silica gel and a copper ion is simultaneously supported on the gel. The resultant copper-containing silica gel is subjected to a reducing treatment in the presence of hydrogen gas.

According to another embodiment of this invention, an aqueous solution containing an ammine complex of copper is mixed with silica gel having an average particle diameter of not more than 200 microns, and the resultant copper-containing silica gel is subjected to reduction. In this embodiment, the hydrogenation catalyst composition of this invention can be obtained by operating in the same way as in the aforesaid embodiment except that the silica gel having an average particle size of not more than 200 microns is used.

The aqueous solution containing an ammine complex of copper can be prepared by a method known per se. For example, it can be prepared by adding ammonia to an aqueous solution containing a copper ion until the solution becomes alkaline. It can also be prepared by adding copper flakes to a concentrated aqueous solution of ammonia and passing air through the mixture.

The aqueous solution containing a copper ion can be obtained by dissolving a water-soluble copper compound (including copper salts) in water. Examples of such copper compounds are copper nitrate, copper sulfate, copper oxalate, copper chloride, copper carbonate, and copper acetate. Cupric nitrate is especially preferred.

The colloidal silica sol is commercially available, and commercial colloidal silica sols can be used in this invention. It can also be prepared by known methods. An example of such methods is described, for example, at pages 331 to 334 of "The Chemistry of Silica", John Wiley & Sons, Inc., New York, 1979.

The silica gel is also commercially available, and commercial silica gel having an average particle diameter of not more than 200 microns or adjusted to this particle size range can be used in this invention. There is no particular restriction on the lower limit of the average particle diameter. For example, its lower limit is preferably about 1 m$\mu$. The preferred average particle diameter is about 5 m$\mu$ to about 150 m$\mu$. The use of silica gel having an average particle diameter of more than 200$\mu$ is undesirable because the amount of copper which can be deposited thereon is small and the resulting catalyst has low activity. There is no special restriction on the method of preparing such silica gel, and the silica gels prepared by any desired method can be utilized. For example, there are available dry methods such as the decomposition of a silicon halide or an organic silicon compound, or reduction of silica sand with coke by heating in arc followed by oxidizing the resultant vapor, and wet method comprising decomposition of sodium silicate with an acid.

For example, the catalyst composition of this invention can be produced by the following procedure.

Such a water-soluble copper compound as exemplified above, for example cupric nitrate, is dissolved in water, and conc. aqueous ammonia is added to the resulting aqueous solution containing a cupric ion until the pH of the mixture reaches at least about 10, for example about 10 to about 12. Thus, a deep blue aqueous solution forms. Silica gel having an average particle diameter of not more than 200$\mu$ or colloidal silica sol is added to the deep blue aqueous solution, and they are stirred to mix and contact them fully with each other. The mixing can be effected either at room temperature or at elevated temperatures, for example at room temperature to about 150° C., under atmospheric or elevated pressures. Elevated temperatures, for example about 40° to about 100° C., are preferred.

The resulting product is subjected, for example, to an evaporating treatment to form a solid residue. As a result, in the former embodiment of using the silica gel, a copper ion is supported on the silica gel having an average particle diameter of not more than 200$\mu$. In the latter embodiment, the silica sol is converted to silica gel and at this stage, a copper ion is supported on the silica gel to form copper-containing silica gel. The resulting solid residue is then washed fully with water and dried. The dried residue is then subjected to a reducing treatment to obtain the catalyst composition of this invention. Instead of the evaporation treatment, a concentrating treatment may be used. For example, the product may be concentrated to about one-half of its original amount, and a solid is recovered from it by, for example, filtration and then treated similarly to the above to obtain the catalyst composition of this invention.

The evaporating treatment and the concentrating treatment may be carried out under atmospheric, reduced or elevated pressures. These treatments can be effected at room temperature or at elevated temperatures. The use of elevated temperatures, for example about 60° to about 90° C., is preferred.

The reducing treatment can be carried out in accordance with a known method by treating the resulting copper-containing silica gel with hydrogen at an elevated temperature. For example, the reducing treatment can be carried out by heat-treating the copper-containing silica gel with hydrogen at about 150° to about 500° C., preferably at about 200° to about 400° C., for abou 1 to about 15 hours. Prior to the reducing treatment, the copper-containing silica gel may be preliminarily heat-treated. For example, the preliminary heat-treatment can be carried out by calcining it in the air at a temperature of about 400° to about 800° C., preferably about 500° to about 750° C., for about 1 to about 10 hours.

In the hydrogenation catalyst composition of this invention obtained as above and composed of a reduction product of copper-containing silica gel formed by contacting an ammine complex of copper with silica gel having an average particle diameter of not more than 200$\mu$ or colloidal silica sol, the weight ratio of $SiO_2$:Cu can be adjusted by properly selecting the amounts of the ammine complex of copper and silica gel or colloidal silica sol during the preparation of the catalyst composition. Preferably, the weight ratio of $SiO_2$:Cu is from 1:about 0.001 to 1: about 2, more preferably from 1:about 0.01 to 1:about 1.

According to this invention, there is provided, in a process for producing a lower alkylene glycol which comprises hydrogenating a lower alkyl ester of a lower hydroxycarboxylic acid in the vapor phase at an elevated temperature in the presence of a hydrogenation catalyst, the improvement wherein the hydrogenation catalyst is the catalyst composition of the present invention composed of a reduction product of copper-containing silica gel formed by contacting an ammine complex of copper with silica gel having an average particle diameter of not more than 200$\mu$ or colloidal silica sol. This process is carried out in a customary manner except that the specific catalyst composition of this invention is used.

The starting alkyl ester of the hydroxycarboxylic acid used in the process of this invention is preferably at least one $C_1$–$C_4$ lower alkyl ester of a $C_2$–$C_5$ lower hydroxycarboxylic acid. Examples of the starting alkyl ester of the hydroxycarboxylic acid include methyl glycolate, ethyl glycolate, propyl glycolate, butyl blycolate, methyl lactate, ethyl lactate, propyl lactate, butyl lactate, methyl α-hydroxybutyrate, ethyl α-hydroxybutyrate, and propyl α-hydroxybutyrate.

The reaction conditions in the presence of the catalyst composition of this invention can be properly selected in accordance with known methods. For example, preferred reaction conditions are as follows:

Reaction temperature

About 140° to about 300° C., preferably about 170° to about 260° C., more preferably about 180° to about 230° C.

Contact time (based on STP)

About 0.01 to about 20 seconds (about 0.02 to about 40 g.sec/ml), preferably about 0.1 to about 3 seconds (about 0.4 to about 10 g.sec/ml).

Reaction pressure

About 0.1 to about 200 atmospheres, preferably about 1 to about 40 atmospheres.

Mole ratio of hydrogen to the hydroxycarboxylate ester

At least 2, preferably about 10 to about 500.

The catalytic hydrogenation reaction of the hydroxycarboxylic acid ester can be carried out in any mode by contacting the hydroxycarboxylic acid ester with hydrogen gas and the catalyst composition in the gaseous or vapor phase in a fixed catalyst bed or a fluidized catalyst bed. The reaction can be carried out either batchwise or continuously.

By hydrogenating the lower hydroxycarboxylic acid ester in this way by using the catalyst obtained by this invention, there can, for example, be obtained ethylene glycol from a glycolic acid ester, propylene glycol from a lactic acid ester, or butanediol from an α-hydroxybutyrate.

The hydrogenating catalyst of the invention does not contain chromium, as is apparent from the method of its preparation. Despite the fact that it does not contain chromium, the catalyst of the invention can efficiently catalyze a reaction of hydrogenating a lower alkyl ester of a lower hydroxycarboxylic acid to a corresponding lower alkylene glycol, and the desired product can be obtained in a higher space time yield than in the case of using the known catalysts.

With many conventional catalysts, the desired product cannot be efficiently produced unless hydrogenation is carried out at a pressure as high as 10 atmospheres or more. In contrast, the use of the catalyst obtained in this invention has the advantage that the desired product can be obtained by performing the hydrogenation at lower pressures than 10 atmospheres.

The following Examples illustrate the present invention more specifically.

EXAMPLE 1

506 g of cupric nitrate trihydrate [$Cu(NO_3)_2.3H_2O$] was dissolved in 1500 ml of water, and 1500 ml of concentrated aqueous ammonia was added to adjust the pH of the solution to about 11–12. Thus, a deep blue solution containing a copper/ammine complex was obtained. The deep blue solution was mixed with a solution obtained by adding 500 ml of water to 666 g of 30% by weight colloidal silica sol. The mixture was stirred at room temperature for several hours. Then, the temperature of the solution was raised to about 85° C. to about 100° C. to evaporate most of water. The mixture was further dried overnight at 120° C. The dried product was thoroughly washed with water, and again dried at 120° C. for 14 hours. The dried product was molded into pellets having a size of 5 mm×5 mmφ, crushed and screened into a size of 9 to 16 mesh, and subjected to a reducing treatment in a stream of hydrogen at 200° C. for 5 hours to prepare a catalyst. The catalyst contained about 40% by weight of copper. The weight ratio of copper to silicon dioxide was about 0.67.

EXAMPLES 2 TO 4

Five milliliters of the catalyst prepared in Example 1 was filled in a stainless steel reaction tube having an inside diameter of 10 mm and a length of 130 mm, and ethyl glycolate was catalytically hydrogenated at an SV of 20000 hr$^{-1}$ and a reaction pressure of 6 kg/cm$^2$.G while maintaining the mole ratio of hydrogen to ethyl glycolate at 100. The reaction temperatures were as indicated in Table 1. The results are shown in Table 1.

TABLE 1

| Example | Reaction temperature (°C.) | Conversion of ethyl glycolate (%) | Selectivity to ethylene glycol (%) |
|---|---|---|---|
| 2 | 180 | 92.0 | 91.4 |
| 3 | 190 | 96.5 | 92.3 |
| 4 | 200 | 100 | 96.0 |

EXAMPLE 5

Five milliliters of the catalyst prepared in Example 1 was filled in a stainless steel reaction tube having an inside diameter of 10 mm and a length of 130 mm, and ethyl lactate was catalytically hydrogenated at an SV of 6000 hr$^{-1}$, a reaction pressure of 6 kg/cm$^2$.G and a reaction temperature of 185° C. while maintaining the mole ratio of hydrogen to ethyl lactate at 60. The results were as follows:

Conversion of ethyl lactate: 98.2%;
Selectivity to propylene glycol: 93.9%.

EXAMPLES 6 AND 7

Twenty-five milliliters of the catalyst prepared in Example 1 was filled in a stainless steel reaction tube having an inside diameter of 19.4 mm and a length of 700 mm, and ethyl glycolate was catalytically hydrogenated at a reaction pressure of 20 kg/cm$^2$.G and an SV of 20000 hr$^{-1}$ while maintaining the mole ratio of hydrogen to ethyl glycolate at 100. The reaction temperatures were as indicated in Table 2. The results are shown in Table 2.

TABLE 2

| Example | Reaction temperature (°C.) | Conversion of ethyl glycolate (%) | Selectivity to ethylene glycol (%) |
|---|---|---|---|
| 6 | 190 | 99.2 | 94.6 |
| 7 | 200 | 100 | 97.5 |

EXAMPLE 8

Cupric nitrate trihydrate (160 g) was dissolved in 600 ml of water, and 500 ml of concentrated aqueous ammonia was added to adjust the pH of the solution to about 11–12. Thus, a deep blue solution containing a copper-ammine complex was obtained. To the deep blue solution was added 562 g of 30% by weight colloidal silica sol, and the mixture was stirred at room temperature for several hours. Then, the temperature was raised to about 85° C. to about 100° C., to evaporate most of water. The mixture was further dried at 120° C. for 12 hours. The dried product was thoroughly washed with water, and again dried in air at 140° C. for 14 hours. The dried product was molded, crushed and screened into a size of 9 to 16 mesh, and subjected to a reducing treatment in a stream of hydrogen at about 200° C. for 5 hours to prepare a catalyst. The catalyst contained about 20% by weight of copper, and the weight ratio of copper to silicon dioxide was about 0.25.

EXAMPLES 9 TO 11

Five milliliters of the catalyst prepared in Example 8 was filled in a stainless steel reaction tube having an inside diameter of 10 mm and a length of 130 mm, and ethyl glycolate was catalytically hydrogenated at a reaction pressure of 6 kg/cm$^2$.G and an SV of 20,000 hr$^{-1}$ while maintaining the mole ratio of hydrogen to ethyl glycolate at 100. The reaction temperatures were as indicated in Table 3. The results are shown in Table 3.

TABLE 3

| Example | Reaction temperature (°C.) | Conversion of ethyl glycolate (%) | Selectivity to ethylene glycol (%) |
|---|---|---|---|
| 9 | 190 | 94.1 | 92.7 |
| 10 | 200 | 98.3 | 94.4 |
| 11 | 210 | 100 | 96.8 |

EXAMPLE 12

Cupric nitrate trihydrate (330 g) was dissolved in 1000 ml of water, and 1000 ml of concentrated aqueous ammonia was added to adjust the pH of the solution to about 11. Thus, a deep blue solution containing a copper-ammine complex was obtained. To the deep blue solution was added 2610 g of 30% by weight colloidal silica sol, and the mixture was stirred at room temperature for 30 to 60 minutes. Then, the temperature was raised to about 85° C. to about 100° C. to evaporate most of water. The mixture was dried at 120° C. for 16 hours. The dried product was thoroughly washed with water, and again dried at 120° C. for 16 hours. The dried product was molded into pellets, crushed and screened into a size of 9 to 16 mesh, and subjected to a reducing treatment at about 200° C. for 5 hours in a stream of hydrogen to prepare a catalyst. The catalyst contained about 10% by weight of copper, and the weight ratio of copper to silicon dioxide was about 0.1.

EXAMPLES 13 AND 14

Five milliliters of the catalyst prepared in Example 12 was filled in a stainless steel reaction tube having an inside diameter of 10 mm and a length of 130 mm, and ethyl glycolate was catalytically hydrogenated at a reaction pressure of 6 kg/cm$^2$.G and an SV of 20,000 hr$^{-1}$ while maintaining the mole ratio of hydrogen to ethyl glycolate at 100. The reaction temperatures were as indicated in Table 4. The results are shown in Table 4.

TABLE 4

| Example | Reaction temperature (°C.) | Conversion of ethyl glycolate (%) | Selectivity to ethylene glycol (%) |
|---|---|---|---|
| 13 | 200 | 79.8 | 93.6 |
| 14 | 210 | 92.4 | 92.9 |

EXAMPLE 15

Twenty-five milliliters of the catalyst prepared in Example 12 was filled in a stainless steel reaction tube having an inside diameter of 19.4 mm and a length of 700 mm, and ethyl glycolate was catalytically hydrogenated at a reaction temperature of 210° C., a reaction pressure of 20 kg/cm$^2$.G and an SV of 19,000 hr$^{-1}$ while maintaining the mole ratio of hydrogen to ethyl glycolate at 60. The results were as follows:
Conversion of ethyl glycolate: 96.9%;
Selectivity to ethylene glycol: 94.8%.

EXAMPLES 16 AND 17

Five milliliters of the catalyst prepared in Example 1 was filled in a stainless steel reaction tube having an inside diameter of 10 mm and a length of 130 mm, and methyl glycolate was catalytically hydrogenated at a reaction pressure of 6 kg/cm$^2$.G and an SV of 20,000 hr$^{-1}$ while maintaining the mole ratio of hydrogen to methyl glycolate at 100. The reaction temperatures were as indicated in Table 5. The results are shown in Table 5.

TABLE 5

| Example | Reaction temperature (°C.) | Conversion of methyl glycolate (%) | Selectivity to ethylene glycol (%) |
|---|---|---|---|
| 16 | 190 | 96.9 | 94.7 |
| 17 | 200 | 100 | 95.1 |

EXAMPLE 18

Pellets (5 mm×5 mmφ) prepared as in Example 1 were calcined in the air at 750° C. for 5 hours. The calcined product was pulverized to a size of 9 to 16 mesh, and subjected to a reducing treatment at 200° C. for 5 hours in a stream of hydrogen to form a catalyst.

EXAMPLES 19 TO 21

Five milliliters of the catalyst prepared in Example 18 was filled in a stainless steel reaction tube having an inside diameter of 10 mm and a length of 130 mm, and ethyl glycolate was catalytically hydrogenated under the same conditions as in Examples 2 to 4.

The results are shown in Table 6.

TABLE 6

| Example | Reaction temperature (°C.) | Conversion of ethyl glycolate (%) | Selectivity to ethylene glycol (%) |
|---|---|---|---|
| 19 | 180 | 93.4 | 93.0 |
| 20 | 190 | 98.1 | 94.6 |
| 21 | 200 | 100 | 95.3 |

COMPARATIVE EXAMPLE 1

Cupric nitrate trihydrate (430 g) was dissolved in 1000 ml of water, and 567 g of 30% silica sol was added little by little while the solution was stirred at room temperature. Then, an aqueous solution of sodium hydroxide obtained by dissolving 143 g of sodium hydroxide in 1000 ml of water was added little by little to form a precipitate. The resultant precipitate was collected by filtration, washed fully with water, and dried in air at 120° C. for 15 hours. The dried product was then molded into pellets, crushed and screened into a size of 9 to 16 mesh, and subjected to a reducing treatment in a stream of hydrogen at 200° C. for 5 hours.

The resulting catalyst contained about 40% by weight of copper, and the weight ratio of copper to silicon dioxide was about 0.67.

COMPARATIVE EXAMPLES 2 TO 4

Five milliliters of the catalyst prepared in Comparative Example 1 was filled in a stainless steel reaction tube having an inside diameter of 10 mm and a length of 130 mm, and ethyl glycolate was catalytically hydrogenated at a reaction pressure of 6 kg/cm$^2$.G and an SV of 20,000 hr$^{-1}$ while maintaining the mole ratio of hydrogen to ethyl glycolate at 100. The reaction temperatures were as indicated in Table 7. The results are shown in Table 7.

TABLE 7

| Comparative Example | Reaction temperature (°C.) | Conversion of ethyl glycolate (%) | Selectivity to ethylene glycol (g) |
|---|---|---|---|
| 2 | 190 | 12.5 | 26.3 |
| 3 | 200 | 20.8 | 33.7 |
| 4 | 210 | 34.1 | 41.9 |

COMPARATIVE EXAMPLE 5

Cupric nitrate trihydrate (24.2 g) was dissolved in 220 ml of water, and a solution of 29.7 g of zinc nitrate [Zn(NO$_3$)$_2$.6H$_2$O] in 270 ml of water was mixed with the resulting solution. Then, a solution of 45.6 g of ammonium chromate [(NH$_4$)$_2$.CrO$_4$] in 140 ml of water was mixed with the mixed solution to give a brown precipitate. Ammonia was added to the solution containing the precipitate to adjust its pH to 7. It was then stirred for 1 to 2 hours to age it, and then filtered. The filtrate was dried at 120° C. for 15 hours. The dried product was put little by little onto a vessel maintained at about 400° C. to decompose it thermally. At this time, the catalyst turned from brown to black. The black catalyst was subjected to a reducing treatment in hydrogen at 200° C. for 5 hours to give a copper-chromium-zinc type catalyst.

COMPARATIVE EXAMPLES 6 TO 8

Five milliliters of the catalyst prepared in Comparative Example 5 was used, and ethyl glycolate was catalytically hydrogenated under the same conditions as in Comparative Examples 2 to 4. The results are shown in Table 8 together with the reaction temperatures used.

TABLE 8

| Comparative Example | Reaction temperature (°C.) | Conversion of ethyl glycolate (%) | Selectivity to ethylene glycol (%) |
|---|---|---|---|
| 6 | 180 | 79.2 | 81.7 |
| 7 | 190 | 88.5 | 84.3 |
| 8 | 200 | 98.0 | 84.6 |

EXAMPLE 22

Cupric nitrate trihydrate (101.2 g) was dissolved in 300 ml of water, and 300 ml of concentrated aqueous ammonia was added to adjust the pH of the solution to about 11-12. Thus, a deep blue solution containing a copper/ammine complex was obtained. A suspension of 40 g of fine particles of silica gel having an average particle diameter of 2.5μ (SYLOID 150, a product of Fuji-Davison Co., Ltd.) in 450 ml of water was added to the deep blue solution, and the mixture was stirred at room temperature for several hours.

Then, the temperature of the mixture was raised to about 85° C. to about 100° C. to evaporate most of water, and the residue was dried further at 120° C. for 12 hours. The dried product was washed fully with water, and dried again in air at 140° C. for 14 hours. The dried product was subjected to a reducing treatment in a stream of hydrogen at 350° C. for 2 to 3 hours to prepare a catalyst. The catalyst contained about 40% by weight of copper, and the weight ratio of copper to silicon dioxide was about 0.67.

EXAMPLES 23 TO 25

Five milliliters of the catalyst prepared in Example 22 was filled in a stainless steel reaction tube having an inside diameter of 10 mm and a length of 130 mm, and ethyl glycolate was catalytically hydrogenated at an SV of 20,000 hr$^{-1}$ and a reaction pressure of 6 kg/cm$^2$.G while maintaining the mole ratio of hydrogen to ethyl glycolate at 100. The reaction temperatures were as indicated in Table 9. The results are shown in Table 9.

TABLE 9

| Example | Reaction temperature (°C.) | Conversion of ethyl glycolate (%) | Selectivity to ethylene glycol (%) |
|---|---|---|---|
| 23 | 180 | 96.7 | 96.5 |
| 24 | 190 | 100 | 93.4 |
| 25 | 200 | 100 | 87.5 |

EXAMPLE 26

Cupric nitrate trihydrate (253 g) was dissolved in 750 ml of water, and 750 ml of concentrated aqueous ammonia was added to adjust the pH of the solution to about 11-12. Thus, a deep blue solution containing a copper-ammine complex was obtained. A suspension prepared by suspending 100 g of ultrafine silica gel having an average particle diameter of 10 to 20 mμ in 1000 ml of water was added to the deep blue solution. The mixture was stirred at room temperature for several hours.

Then, the temperature of the mixture was raised to about 85° to about 100° C. to evaporate most of water. The residue was further dried at 120° C. for 16 hours. The dried product was fully washed with water, again dried at 120° C. for 24 hours, and subjected to a reducing treatment in a stream of hydrogen at 200° C. for 12 hours to prepare a catalyst. The catalyst contained about 40% by weight of copper, and the weight ratio of copper to silicon dioxide was about 0.67.

EXAMPLES 27 TO 29

Five milliliters of the catalyst prepared in Example 26 was filled in a stainless steel reaction tube having an inside diameter of 10 mm and a length of 130 mm, and ethyl glycolate was catalytically hydrogenated at a reaction pressure of 6 kg/cm$^2$.G and an SV of 20,000 hr$^{-1}$ while maintaining the mole ratio of hydrogen to ethyl glycolate at 100. The reaction temperatures were as indicated in Table 10. The results are shown in Table 10.

TABLE 10

| Example | Reaction temperature (°C.) | Conversion of ethyl glycolate (%) | Selectivity to ethylene glycol (%) |
|---|---|---|---|
| 27 | 190 | 96.8 | 92.9 |
| 28 | 200 | 100 | 84.7 |
| 29 | 210 | 100 | 68.0 |

EXAMPLE 30

Five milliliters of the catalyt prepared in Example 22 was filled in a stainless steel reaction tube having an inside diameter of 10 mm and a length of 130 mm, and ethyl lactate was catalytically hydrogenated at an SV of 6000 hr$^{-1}$, a reaction pressure of 6 kg/cm$^2$.G and a reaction temperature of 185° C. while maintaining the mole ratio of hydrogen to ethyl lactate at 60. The conversion of ethyl lactate was 96.2%, and the selectivity to propylene glycol was 90.5%.

EXAMPLE 31

Fifty grams of cupric nitrate trihydrate was dissolved in 150 ml of water, and 200 ml of concentrated aqueous ammonia was added to adjust the pH of the solution to about 11-12. Thus, a deep blue solution containing a copper-ammine complex was obtained. To the deep blue solution was added 19.2 g of fine silica gel particles having an average particle diameter of 100μ, and the mixture was stirred at room temperature for several hours.

Then, the temperature of the mixture was raised to about 85° to about 100° C. to evaporate most of water. The residue was further dried at 120° C. for 16 hours. The dried product was fully washed with water, again dried at 120° C. for 24 hours, and subjected to a reducing treatment in a stream of hydrogen at 200° C. for 12 hours to prepare a catalyst. The catalyst contained about 40% by weight of copper, and the weight ratio of copper to silicon dioxide was about 0.67.

EXAMPLES 32 AND 33

Twenty-five milliliters of the catalyst prepared in Example 31 was filled in a stainless steel reaction tube having an inside diameter of 19.4 mm and a length of 700 mm, and ethyl glycolate was catalytically hydrogenated at a reaction pressure of 20 kg/cm$^2$.G and an SV of 20,000 hr$^{-1}$ while maintaining the mole ratio of hydrogen to ethyl glycolate at 100. The reaction temperatures were as indicated in Table 11. The results are shown in Table 11.

TABLE 11

| Example | Reaction temperature (°C.) | Conversion of ethyl glycolate (%) | Selectivity to ethylene glycol (%) |
|---|---|---|---|
| 32 | 190 | 98.2 | 93.5 |
| 33 | 200 | 100 | 96.2 |

COMPARATIVE EXAMPLE 9

A catalyst was prepared by the same operation as in Example 31 except that 19.2 g of silica gel having an average particle diameter of 250μ was used instead of the silica gel having an average particle diameter of 100μ. The catalyst contained about 40% by weight of copper, and the weight ratio of copper to silicon dioxide was about 0.67.

COMPARATIVE EXAMPLES 10 TO 12

Five milliliters of the catalyst prepared in comparative Example 9 was filled in a stainless steel reaction tube having an inside diameter of 10 mm and a length of 130 mm, and ethyl glycolate was catalytically hydrogenated at a reaction pressure of 6 kg/cm$^2$.G and an SV of 20,000 hr$^{-1}$ while maintaining the mole ratio of hydrogen to ethyl glycolate at 100. The reaction temperatures were as indicated in Table 12. The results are shown in Table 12.

TABLE 12

| Comparative Example | Reaction temperature (°C.) | Conversion of ethyl glycolate (%) | Selectivity to ethylene glycol (%) |
|---|---|---|---|
| 10 | 190 | 12.4 | 25.8 |
| 11 | 200 | 19.8 | 33.7 |
| 12 | 210 | 34.1 | 40.2 |

What is claimed is:

1. A process for producing a lower alkylene glycol, which comprises hydrogenating a lower alkyl ester of a lower hydroxycarboxylic acid in the vapor phase at an elevated temperature in the presence of a hydrogenation catalyst composition composed of a reduction product of copper-containing silica gel formed by contacting an ammine complex of copper with silica gel having an average particle diameter of not more than 200 microns or colloidal silica sol.

2. The process of claim 1 wherein the alkyl ester is a $C_1$–$C_4$ alkyl ester of a $C_2$–$C_5$ hydroxycarboxylic acid.

3. The process of claim 1 wherein the elevated temperature is about 140° C. to about 300° C.

4. The process of claim 1 wherein the mole ratio of hydrogen to the lower alkyl ester of a lower hydroxycarboxylic acid is at least 2.

5. The process of claim 1 wherein said hydrogenation catalyst composition is composed of the reduction product of copper-containing silica gel formed by contacting an ammine complex of copper with silica gel having an average diameter of not more than 200 microns.

6. The process of claim 1 wherein the copper-containing silica gel is formed by contacting an ammine complex of copper with colloidal silica sol.

7. The process of claim 1 wherein the weight ratio of SiO$_2$ to Cu in said hydrogenation catalyst composition is from 1:about 0.001 to 1:about 2.

8. The process of claim 1 wherein the silica gel has an average particle diameter of at least 1 micron.

9. The process of claim 1 wherein the weight ratio of $SiO_2$:Cu is from about 1:about 0.01 to 1:about 1.

10. The process of claim 1 wherein the silica gel has an average particle diameter of from about 5 to 150 microns.

11. The process of claim 1 wherein the vapor phase hydrogenation is carried out at a reaction pressure of about 0.1 to about 200 atmospheres.

12. The process of claim 1 wherein the vapor phase hydrogenation is carried out at a reaction pressure of from about 1 to 40 atmospheres.

13. The process of claim 12 wherein the elevated temperature is from about 170° to about 260° C.

14. The process of claim 1 wherein the vapor phase hydrogenation is carried out at a pressure of less than about 10 atmospheres.

* * * * *

UNITED STATES PATENT AND TRADEMARK OFFICE
CERTIFICATE OF CORRECTION

PATENT NO. : 4,511,744
DATED : April 16, 1985
INVENTOR(S) : MIYAZAKI, ET AL.

It is certified that error appears in the above-identified patent and that said Letters Patent is hereby corrected as shown below:

On the title page;

Assignee: Please delete "UISE Industries, Ltd.", insert --UBE Industries, Ltd.--

Signed and Sealed this

Twenty-third Day of July 1985

[SEAL]

Attest:

DONALD J. QUIGG

Attesting Officer  Acting Commissioner of Patents and Trademarks